United States Patent [19]

Roark et al.

[11] Patent Number: 4,942,267

[45] Date of Patent: Jul. 17, 1990

[54] PERCHLOROETHYLENE STABILIZATION

[75] Inventors: Roger W. Roark; Glenn R. Cairns, both of Painesville; Edward A. Rowe, Jr., North Perry, all of Ohio

[73] Assignee: Occidential Chemical Corporation, Niagara Falls, N.Y.

[21] Appl. No.: 225,580

[22] Filed: Jul. 28, 1988

Related U.S. Application Data

[63] Continuation of Ser. No. 945,167, Dec. 22, 1986, abandoned, which is a continuation of Ser. No. 529,987, Sep. 9, 1983, abandoned, which is a continuation of Ser. No. 320,614, Nov. 12, 1981, abandoned.

[51] Int. Cl.$^5$ .................... C07C 17/42; C07C 21/12
[52] U.S. Cl. ........................... 570/109; 134/31
[58] Field of Search ............. 570/121, 109, 118, 172

[56] References Cited

U.S. PATENT DOCUMENTS

| | | |
|---|---|---|
| 2,111,253 | 3/1938 | Stoesser et al. ............... 570/109 |
| 3,269,953 | 8/1966 | Boothman ....................... 570/109 |
| 3,291,745 | 12/1966 | Morton ............................ 252/171 |
| 3,424,805 | 1/1969 | Fruhwirth et al. ............. 260/652.5 |
| 3,642,645 | 2/1972 | Schmidhammer ............. 252/162 |
| 3,742,075 | 6/1973 | Mayer-Mader et al. ....... 570/103 |
| 3,868,426 | 2/1975 | Kleiman ......................... 252/399 |
| 4,378,968 | 4/1983 | Peignier et al. ................ 570/118 |

FOREIGN PATENT DOCUMENTS 20968 9/1969 Japan .................................. 570/108

*Primary Examiner*—J. E. Evans
*Attorney, Agent, or Firm*—James F. Tao; Richard D. Fuerle; William G. Gosz

[57] ABSTRACT

Decomposition of perchloroethylene is prevented by the addition of a stabilizer system containing N-substituted cyclic alkyl amine, alcohol of 3–7 carbon atoms and olefin components. The stabilizer system is advantageous in that it does not contain any environmentally undersirable materials.

8 Claims, No Drawings

PERCHLOROETHYLENE STABILIZATION

This application is a continuation of application S.N. 06/945,167 filed 12/22/86, abandoned, which is a continuation of application S.N. 06/529,987 filed 09/09/83, abandoned, which is a continuation of application S.N. 06/320,614 filed 11/12/81, abandoned.

FIELD OF THE INVENTION

This invention relates generally to the stabilization of chlorinated hydrocarbons, and more specifically to the stabilization of perchloroethylene with a composition which is free of epoxides.

BACKGROUND OF THE INVENTION

Perchloroethylene (tetrachloroethylene) is a widely used industrial solvent. It is used extensively as a degreasing solvent, particularly in vapor phase degreasing where the article to be cleaned is suspended over a boiling sump of perchloroethylene and the suspended article is cleaned by condensation of perchloroethylene vapors on its surface. Perchloroethylene tends to decompose in the presence of oxygen, heat, light, metals, metal salts, organic materials and other contaminants to which it is exposed during storage and use in degreasing operations. Decomposition of perchloroethylene adversely affects its desirable properties as well as its useful life as a solvent.

It is known that the decomposition of perchloroethylene can be minimized or prevented by the addition of small quantities of various chemical components which act as stabilizers. These components are often combinations of two or more different types of chemical compounds and are known as stabilizer systems. For example, the acid materials produced as a result of the decomposition reaction can be bound by the use of agents such as amines, and oxidation reactions can be retarded by phenols, so these types of materials are often added in combination. The epoxide compounds, such as epichlorohydrin, glycidol, glycidyl ethers and the like, have also been widely used in the most effective perchloroethylene stabilizer systems. The epoxides are compounds incorporating the oxirane structure, a three membered ring containing one oxygen atom and two carbon atoms.

Epichlorohydrin is the most commonly used epoxide compound due to its ready availability and proven effectiveness in stabilizer systems. However, epichlorohydrin has been demonstrated to exhibit mutagenic activity. The continued use of epoxide compounds in perchloroethylene stabilization has therefore become questionable, and the development of an effective stabilizer system which is free of epoxides would be desirable.

SUMMARY OF THE INVENTION

It has now been discovered that perchloroethylene can be stabilized against decomposition by adding an effectively stabilizing amount of a mixture of N-substituted cyclic alkyl amine, an alcohol of 3-7 carbon atoms and an olefin. This stabilizer system does not contain any environmentally undesirable components, yet it has been demonstrated to prevent the decomposition of perchloroethylene even under the extreme conditions of heat, vaporization, metal contact and contamination which are encountered in degreasing operations.

DESCRIPTION OF THE INVENTION

In preparing the stabilizer system of the invention, the amine component is selected from the N-substituted cyclic alkyl amines. Suitable compounds of this type include N,N'-dimethylpiperazine, N,N'-diethylpiperazine, N-methylpiperazine and N-ethylpiperazine. Due to the desirability of maintaining a reasonably uniform distribution of stabilizer between the liquid and vapor phases of the perchloroethylene, the N-substituted cyclic alkyl amines which have a boiling point between about 130° C. and about 140° C. are preferred. Of these materials, the N,N'-dimethylpiperazine is particularly preferred.

The quantity of the amine component of the stabilizer system which is required will of course vary with the stress or workload to which the perchloroethylene is subjected. An effectively stabilizing amount of the stabilizer system is best achieved by including from about 0.05 to about 0.25 percent by weight of amine in the perchloroethylene. Satisfactory stabilization will normally be realized by maintaining the amine concentration in the range of 0.05 to 0.10 percent by weight based on the perchloroethylene.

The alcohol component of the stabilizer system is selected from alcohols containing 3 to 7 carbon atoms, either acyclic or cyclic. Representative alcohols include n-butanol, n-pentanol, cyclopentanol, cyclohexanol, 2-methoxyethanol, 2-methyl-3-butane-3-ol, 3-methyl-1-pentyne-3-ol and 2,3-butanediol. Mixtures of several alcohols may be used to make up the alcohol component.

Once again, in order to obtain optimum distribution of the stabilizer between the liquid and vapor phases of the perchloroethylene, it is desirable to use an alcohol or mixture of alcohols with a boiling point below about 140° C. The most preferred boiling range is between about 110° C. and about 140° C.

The amount of alcohol component added to the perchloroethylene ranges from about 0.01 to about 0.2 percent by weight of the solvent. The preferred range of alcohol is usually from 0.05 to 0.10 percent by weight based on the perchloroethylene. Larger quantities of each of the components in the stabilizer system of the invention may of course be used, but the stabilizing effect is normally not enhanced and the increased cost of the stabilizer system can seldom be justified.

The olefin component of the system may be selected from materials such as 1-octene, 1-decene, dicyclopentadiene, 1,3,5-cycloheptatriene, 2-ethyl-2-oxazoline and 1,5-cyclooctadiene. As the olefin component is most effective in preventing decomposition of the perchloroethylene in the liquid phase, it is desirable to maintain the majority of the olefin in this phase. Therefore, olefins, or mixtures of olefins, having a boiling point above about 140° C. are preferred.

The olefin component is usually added to the perchloroethylene in an amount from about 0.01 to about 0.2 percent by weight. The preferred range is from 0.04 to 0.06 percent by weight of the perchloroethylene.

The synergistic combination of amine, alcohol and olefin in the stabilizer system of the invention is surprisingly effective in preventing the decomposition of perchloroethylene, even in the absence of an epoxide stabilizer. However, in view of the wide range of conditions to which perchloroethylene is exposed during its use and the variety of contaminants encountered, it may be desirable to use the stabilizer system of the invention in combination with other stabilizers. Other stabilizers may provide a different type of stabilization or may enhance the action of the system of the invention. Useful classes of stabilizers which are compatible with the system of the invention include aliphatic and aromatic amines, nitrogen containing materials such as pyrroles, cyclic ethers (which are not epoxides) and aromatic compounds containing a phenol group.

The invention is further illustrated by the following examples, which should not be construed in any limiting sense.

EXAMPLE 1

The stabilizer system of the invention was evaluated in a commercial vapor degreaser, which consists of an open 600 gallon steel tank charged with about 110 gallons of perchloroethylene with a heated solvent reservoir or sump at the bottom and a cooling coil near the top of the tank. Sufficient heat is introduced into the sump to boil the perchloroethylene solvent and generate vapor. Since the hot solvent vapor is heavier than air, it displaces the air and fills the tank up to the cooling zone. The hot vapor condenses when it reaches the cooling zone, thus maintaining a fixed vapor level and creating a thermal balance. Metal parts or workpieces to be cleaned are lowered into the vapor, where the relative coolness of the workpiece causes liquid solvent to condense on its surface. The condensate dissolves the soil or grease and removes it from the surface by dripping back into the liquid sump. When the workpiece reaches the temperature of the hot vapor, condensation and cleaning cease and the dry workpiece is removed from the tank.

The commercial degreaser was charged with perchloroethylene containing a stabilizer system consisting of N,N'-dimethylpiperazine (0.06 percent by weight based on perchloroethylene), 2-methoxyethanol (0.10 percent by weight) and dicyclopentadiene (0.05 percent by weight). The stock perchloroethylene to which the stabilizer system of the invention was added contained minor amounts of storage stabilizer, namely 20 ppm of N-methyl pyrrole and 50 ppm of p-tertiary amyl phenol, which did not affect the degreasing stability test.

The degreaser was operated for a five week period, eight hours each weekday and four hours on Saturdays. The bath was replenished with about 10 gallons of stabilized perchloroethylene each day to make up for evaporation losses. The composition of the workload was stainless steel, aluminum and brass in varying quantities, but the demand on the degreaser solvent was consistently high.

Samples were taken from the sump and the condensate trough of the degreaser on alternate workdays. These were analyzed for concentration of the stabilizer system components by gas chromatography, and for alkalinity by acid-base titration. The results of these tests are set forth in Table I.

TABLE I

| | WORKDAY | | | | | | | | | | | |
|---|---|---|---|---|---|---|---|---|---|---|---|---|
| | 0 | 3 | 5 | 7 | 9 | 12 | 14 | 16 | 18 | 20 | 22 | 25 |
| N,N'-dimethylpiperazine (%) | | | | | | | | | | | | |
| Liquid phase | .06 | .035 | .029 | .021 | .015 | .015 | .013 | .020 | .020 | .014 | .023 | .021 |
| Vapor Phase | — | .031 | .015 | .013 | .011 | .013 | .007 | .009 | .010 | .018 | .012 | .018 |
| 2-methoxyethanol (%) | | | | | | | | | | | | |
| Liquid phase | .10 | .022 | .020 | .013 | .020 | .018 | .018 | .027 | .024 | .019 | .029 | .027 |
| Vapor phase | — | .035 | .033 | .025 | .014 | .014 | .015 | .033 | .037 | .050 | .050 | .063 |
| Dicyclopentadiene (%) | | | | | | | | | | | | |
| Liquid phase | .05 | .044 | .039 | .035 | .045 | .048 | .044 | .048 | .040 | .030 | .043 | .038 |
| Vapor phase | — | .014 | .009 | .011 | .013 | .015 | .011 | .009 | .010 | .015 | .012 | .016 |
| Alkalinity (ppm as NaOH) | 210 | 106 | 116 | 86 | 94 | 54 | 49 | 42 | 37 | 25 | 44 | 36 |
| pH | | | 9.0 | | | 8.8 | | | 8.7 | | | 8.4 |

The distribution of the stabilizer components remained stable throughout the test period. The degreasing operation was trouble free and no evidence of decomposition of the perchloroethylene was observed, as indicated by the continued alkalinity of the solvent. Degreasing of the workload was satisfactory throughout the test period.

One of the disadvantages of perchloroethylene as a solvent in vapor degreasing is that appreciable quantities of the solvent and stabilizers may be lost by evaporation, particularly if the workload is heavy and the vaporization in the sump is maintained at a high rate. If disproportionate amounts of the stabilizer components are lost, the system may no longer provide satisfactory protection. However, as seen from the results of the commercial test, the stability of perchloroethylene containing effective amounts of the stabilizer system of the invention was not adversely affected even after considerable evaporation.

EXAMPLES 2-15

A series of stabilizer systems of the invention were evaluated using a "72 hour stability test," which comprises placing 100 ml of the stabilized perchloroethylene into a flask fitted with a Soxhlet extractor and condenser together with 0.2 ml of distilled water. Three strips of weighed 0.003 gauge steel 2.0 by 7.5 cm in size were located as follows: one strip in the solvent in the flask; the second strip in the Soxhlet extractor; and the third strip in the lower end of the condenser. A 100w incandescent light bulb was located one inch from the vapor tube of the Soxhlet extractor. Heat was applied to the flask at a rate sufficient to cause the extractor to siphon every 8-10 minutes. Refluxing was continued for 72 hours, at which time the light and heat were turned off and the solvent allowed to cool. The steel strips were removed, cleaned of any corrosion and reweighed. The total loss due to the corrosive effect of the perchloroethylene was calculated. This weight loss is a reflection of both the extent of decomposition of the solvent and its resulting corrosive effect.

The results of the stability test for various combinations of the components of the system are set forth in Table II. The effectiveness of the stabilizer system of the invention, in comparison to the effectiveness of the individual components, is clearly shown by the results. The stock perchloroethylene used in the tests was storage stabilized as described in Example 1.

TABLE II

| | EXAMPLE | | | | | | | | | | | | | |
|---|---|---|---|---|---|---|---|---|---|---|---|---|---|---|
| | 2 | 3 | 4 | 5 | 6 | 7 | 8 | 9 | 10 | 11 | 12 | 13 | 14 | 15 |
| AMINE | | | | | | | | | | | | | | |
| N,N'-dimethylpiperazine (%) | .05 | .05 | .05 | .05 | .025 | .05 | .10 | .05 | | | | | | |
| ALCOHOL | | | | | | | | | | | | | | |
| n-butanol | .05 | .025 | | | | | | | .05 | | | | | |
| n-pentanol | | | | | .05 | | | | | .05 | | | | |
| cyclohexanol | | | | | | .05 | | | | | .05 | | | |
| 2-methoxyethanol | | | | .05 | | | .05 | | | | | .05 | | |
| 2,3-butanediol | | .025 | .05 | | | | | | | | | | | |
| OLEFIN | | | | | | | | | | | | | | |
| dicyclopentadiene | .05 | .05 | .05 | .05 | | .05 | .05 | | | | | | .05 | |
| 1-octene | | | | | .05 | | | | | | | | | .075 |
| 1-decene | | | | | .05 | | | | | | | | | .075 |
| Total Metal Loss (mg) | 26 | 18 | 48 | 65 | 110 | 37 | 25 | 141 | 301 | 257 | 290 | 259 | 243 | 305 |

What is claimed is:

1. A stabilized perchloroethylene composition comprising perchloroethylene and a stabilizing amount of a mixture entirely free of any compound that contains an oxirane ring and consisting essentially of
    (a) an amine component selected from the group consisting of N,N'-dimethylpiperazine, N,N'-diethylpiperazine, N-methylpiperazine, N-ethylpiperazine, and mixtures thereof;
    (b) an alcohol component selected from the group consisting of n-butanol, n-pentanol, cyclohexanol, 2-methoxyethanol, 2,3-butanediol, and mixtures thereof; and
    (c) an olefin component selected from the group consisting of 1-octene, 1-decene, 1,3,5-cycloheptatriene, dicyclopentadiene, and mixtures thereof.

2. The composition of claim 1 wherein said amine component is N,N'-dimethylpiperazine, said alcohol component is 2-methoxyethanol, and said olefin component is dicyclopentadiene.

3. The composition of claim 1 wherein the amount of said amine component is 0.05 to 0.1 percent by weight, the amount of said alcohol component is 0.05 to 0.1 percent by weight, and the amount of said olefin component is 0.04 to 0.06 percent by weight.

4. A process for the stabilization of perchloroethylene, which comprises forming a stabilized perchloroethylene composition entirely free of any compound that contains an oxirane ring by adding to perchloroethylene an effectively stabilizing amount of a mixture comprising
    (a) an amine component selected from the group consisting of N,N'-dimethylpiperazine, N,N'-diethylpiperazine, N-methylpiperazine, N-ethylpiperazine, and mixtures thereof;
    (b) an alcohol component selected from the group consisting of n-butanol, n-pentanol, cyclohexanol, 2-methoxyethanol, 2,3-butanediol, and mixtures thereof; and
    (c) an olefin component selected from the group consisting of 1-octene, 1-decene, 1,3,5-cycloheptatriene, dicyclopentadiene, and mixtures thereof.

5. The composition of claim 1 wherein the amount of said amine component is about 0.05 to about 0.25 percent by weight, the amount of said alcohol component is about 0.01 to about 0.2 percent by weight, and the amount of said olefin component is about 0.01 to about 0.02 percent by weight.

6. A process according to claim 4 wherein said amine component is N,N'-dimethylpiperazine, said alcohol component is 2-methoxyethanol, and said olefin component is dicyclopentadiene.

7. A process according to claim 4 wherein the amount of said amine component is about 0.05 to about 0.25 percent by weight, the amount of said alcohol component is about 0.01 to about 0.2 percent by weight, and the amount of said olefin component is about 0.01 to about 0.02 percent by weight.

8. A process according to claim 4 wherein the amount of said amine component is 0.05 to 0.1 percent by weight, the amount of said alcohol component is 0.05 to 0.1 percent by weight, and the amount of said olefin component is 0.04 to 0.06 percent by weight.

* * * * *